Figure 1:
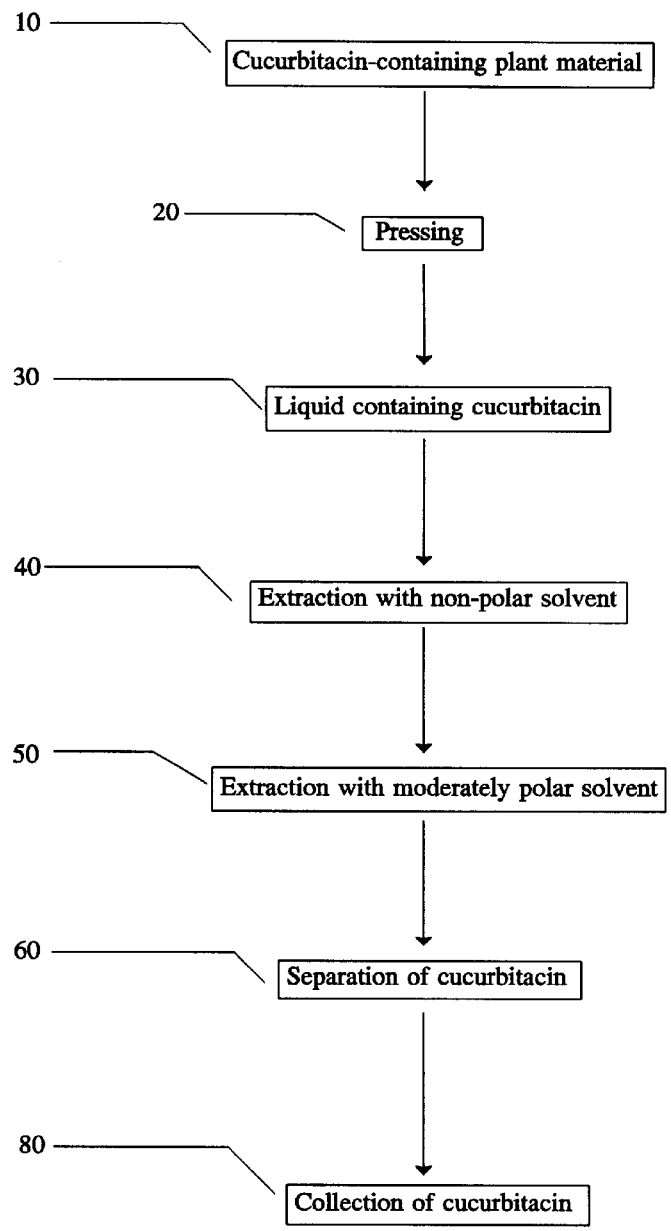

United States Patent [19]
Subbiah

[11] Patent Number: 5,925,356
[45] Date of Patent: Jul. 20, 1999

[54] METHOD OF ISOLATING CUCURBITACIN

[76] Inventor: Ven Subbiah, 105 Bella Vista Dr., Edenton, N.C. 27932

[21] Appl. No.: 08/680,518

[22] Filed: Jul. 9, 1996

[51] Int. Cl.$^6$ .......................... A01N 65/00; A01N 25/00; C07C 7/00

[52] U.S. Cl. ...................... 424/195.1; 585/802; 585/947; 424/84

[58] Field of Search .................................... 424/84, 195.1, 424/205, 206; 585/947, 800, 802; 260/1

[56] References Cited

U.S. PATENT DOCUMENTS

| | | | |
|---|---|---|---|
| 4,764,372 | 8/1988 | Herrnstadt et al. | 424/93.461 |
| 4,880,624 | 11/1989 | Metcalf et al. | 424/84 |
| 5,466,460 | 11/1995 | McMahon et al. | 424/408 |
| 5,484,587 | 1/1996 | Branly et al. | 424/84 |

FOREIGN PATENT DOCUMENTS

| | | |
|---|---|---|
| 1195922 | 10/1985 | Canada . |
| 2024085 | 5/1991 | Canada . |

OTHER PUBLICATIONS

Halaweish, "Cucurbitacins from *Cucurbita texana*: evidence for the role of isocucurbitacins", J. chem. Ecol. (1993) vol. 19(1), pp. 29–37, 1993.

Doskotch et al. "Cucurbitacin B, the cytotoxic principle of *Begonia tuberhybrida* var. *alba*", Lloydia (1969) vol. 32(2), pp. 115–122, Jun. 1969.

Hatam et al. "Cucurbitacin glycosides from *Citrullus colocynthis*", Phytochemistry (1989) vol. 28(4) pp. 1268–1271, 1989.

Robert L. Metcalf et al., "Cucurbitacins as kairomones for diabroticite beetles", Procedure of the National Academy of Science USA, vol. 77, No. 7, pp. 3769–3772 (Jul. 1980).

Christopher J. DeHeer et al., "Affinity of Spotted Cucumber Beetle (Coleoptera: Chrysomelidae) Larvae to Cucurbitacins", Environmental Entomology, vol. 20, No. 4, pp. 1173–1175 (Aug. 1991).

P.M. Gorski et al., "Rapid TLC and HPLC Quantification of Cucurbitacin C in Cucumber Cotyledons", Hortscience, vol. 21, No. 4, pp. 1034–1036 (Aug. 1986).

Douglas W. Tallamy et al., "Variation and Function of Cucurbitacins in Cucurbita: An Examination of Current Hypotheses", The American Naturalist, vol. 133, No. 6, pp. 766–786 (Jun. 1989).

J. Guha et al., "The Cucurbitacins—A Review", The Plant Biochemical Journal, vol. 2, No. 1, pp. 12–28 (Sep. 1975).

Douglas W. Tallamy et al., "Effects of Age, Reproductive Activity, Sex, and Prior Exposure on Sensitivity to Cucurbitacins in Southern Corn Rootworm (Coleoptera: Chrysomelidae)", Environmental Entomology, vol. 22, No. 5, pp. 925–932 (May 1993).

J. Russell Mason et al., "Cucurbitacin–Adulterated Diet is Avoided By Captive European Starlings", Journal of Wildlife Management, vol. 54, No. 4, pp. 672–676 (May 1990).

John M. Cassady (Editor), Anticancer Agents Based on Natural Product Models, Academic Press (1980), pp. 247–254 (V. Cucurbitacins).

Bert L. Bohmont, The Standard Pesticide User's Guide, Revised and Enlarged, Prentice Hall (1990), pp. 223–255 (10. Pesticide Formulations and Adjuvants).

M.E. Barbercheck et al., "Evaluation of Semiochemical Baits for Management of Southern Corn Rootworm (Coleoptera: Chrysomelidae) in Peanuts", Journal of Economic Entomology, vol. 88, No. 6, pp. 1754–1763 (Jul. 1995).

W. Clark Still et al., "Rapid Chromatographic Technique for Preparative Separations with Moderate Resolution", Journal of Organic Chemistry, vol. 43, No. 14, pp. 2923–2925 (Jan. 1978).

Douglas A. Skoog et al., "Method Development in Partition Chromatography", Principles of Instrumental Analysis, Fourth Edition, Saunders College Publishing (1992), pp. 644–647.

M. Miro, "Cucurbitacins and their Pharmacological Effects", (Review Paper—10 pp.) Department of Pharmacology, Faculty of Pharmacy, University of Granada, Granada, Spain.

Scopes, R. "Protein Purificaiton: Principles and Practice", 2nd edition. 1987) (Springer–Verlag: New York) pp. 21–37, 1987.

Casey et al. "Advanced Practical Organic Chemistry", (1990) (Chapman and Hall: New York) pp. 166–177, 1990.

*Primary Examiner*—Jean C. Witz
*Assistant Examiner*—Susan Hanley
*Attorney, Agent, or Firm*—Myers Bigel Sibley & Sajovec

[57] ABSTRACT

A method of isolating and purifying cucurbitacin is described. The method involves providing a cucurbitacin-containing liquid obtained from plant matter containing cucurbitacin, which liquid is then sequentially extracted with a non-polar solvent and then a moderately polar solvent. In a preferred embodiment, the cucurbitacin is purified by flash-column chromatography.

7 Claims, 2 Drawing Sheets

METHOD OF ISOLATING CUCURBITACIN

FIELD OF THE INVENTION

The present invention relates to methods for isolating and purifying triterpenic substances from plants.

BACKGROUND OF THE INVENTION

In the United States, rootworms and cucumber beetles cause considerable damage to corn, soybeans, cucurbits (e.g. squashes, melons, gourds, pumpkins) and other crops. R. L. Metcalf and W. H. Luckman, *Introduction to Insect Pest Management*, 3rd Ed., p. 328 (1994). Control practices over the last several decades have largely relied on heavy applications of soil and foliage insecticides. Unfortunately, the application of large amounts of insecticides has led to resistance to the compounds in target insects, accelerated microbial degradation, and the widespread pollution of groundwater due to pesticide run-off. Id. Additionally, there has been a progression in usage from the relatively inexpensive organochlorine insecticides to the increasingly expensive organophosphate, carbamate, and pyrethyroid insecticides. Thus, the cost of pest management has increased dramatically. Id.

In recent years, one strategy for combatting insect infestation has been the use of insect attractants, arrestants and phagostimulants in combination with smaller quantities of insecticides. Generally, this strategy involves the use of a formulation containing one or more insect-specific phagostimulants or attractants, along with a low concentration of a pesticide toxic to that insect. After application of the formulation to crops targeted by the insect, the insects are attracted to the formulation and induced to feed, but are then killed by the insecticide.

This strategy has particular potential in the management of Diabroticite rootworms and related species. There are more than 1400 species of Diabroticites worldwide, many of which are serious pests of corn, peanuts, cucurbits, and sugarbeets in North and South America, Africa, Asia and Australia. These insects have co-evolved with plants of the family Cucurbiticae and have developed specific host-plant recognition signals for the toxic cucurbitacins characteristic of this family.

The cucurbitacins are a group of bitter-tasting, highly oxygenated, mainly tetracyclic, triterpenic plant substances derived from the cucurbitane skeleton. M. Miro, *Phytother. Res.* 8, 159–168 (1995). These compounds are present in many plants and function as an allomone to protect the plants from herbivores. R. L. Metcalf, *J. Chem. Ecol.* 12, 1109–1124 (1986). In addition, the cucurbitacins are known to have purgative, anti-inflammatory, anti-fungal, and anti-cancer properties. See M. Miro et al., *Phytother. Res.* 9, 159–68 (1994); *Anticancer Agents Based on Natural Product Models* pp. 247–254 (J. M. Cassady and J. D. Dourous, eds., Academic Press, New York, 1980).

Diabroticite beetles are known to compulsively consume plant tissue of the Cucurbitale order. When consumed by the beetles, the cucurbitacins are sequestered in the wings, and are thereby believed to act as predation deterrents. In addition to their properties as diabroticite phagostimulants, cucurbitacins also function as anti-feedants for other families of insects, and for other herbivorous pests such as birds. Cucurbitacins are among the most bitter compounds known, and in nanogram quantities deter most non-Diabrotic herbivores. Additionally, high concentrations of cucurbitacins are toxic to certain insect, bird and mammalian species.

Commercialization of cucurbitacin-based products has been very limited because (a) the triterpenes are secreted in very small quantities in cucurbitaceous plants, and (b) the existing procedures involved in obtaining pure cucurbitacins is lengthy and burdensome. See, F. T. Halaweish and D. W. Tallamy, *J. Liquid Chromatography* 16, 497–511 (1993); J. Guha and S. P. Sen, *Plant Biochemical Journal* 2, 12–28 (1975). The difficulties involved in obtaining large quantities of cucurbitacins in the past has discouraged the serious pursuit of most potential uses of this triterpenes.

U.S. Pat. No. 5,466,460 to McMahon et al. describes controlled-release microcapsules that contain insecticides and other compounds useful in crop management. In one embodiment of the invention, the capsule wall contains an anti-feedant compound comprising cucurbitacin-containing solid particles, powder or dust. The preferred cucurbitacin-containing solids used are in the form of dried, ground, gourd roots as described in U.S. Pat. No. 4,880,624.

U.S. Pat. No. 5,484,587 to Branly et al. describes baits for diabroticite beetles containing a feeding stimulant and an insecticide. The feeding stimulant comprises plant tissue containing cucurbitacin, and more specifically comprises dried buffalo gourd root in an amount of 10–100 lb. of ground root per acre.

Based upon the above-described technology, a cucurbitacin-dependent control method for adult cucumber beetles has reportedly been developed. By lacing cucurbitacin-containing plant tissue with insecticide, the beetles are "tricked" by the feeding-stimulant cucurbitacins into eating the toxins. This method is pest-specific and constitutes a point-source or broadcasted bait capable of killing 99% of the beetles consuming it. See, R. L. Metcalf et al., *J. Econ. Entomol.* 80, 870–875 (1987); D. R. Lance and G. R. Sutter, *J. Econ. Entomol.* 83, 1085–1090 (1990); *J. Econ. Entomol.* 84, 1861–1868 (1991). Additionally, the method uses as little as less than 10% of the insecticide quantity per unit area required for conventional insect control. However, the method has achieved only limited success due to the use of ground root tissue as the cucurbitacin source, in that it appears that this form of cucurbitacin is effective in the control of adult beetles only, while much of the damage caused by the diabroticite beetles is caused by the larval form. See, B. P. Spike and J. J. Tollefson, *J. Econ. Entomol.* 84, 1585–1590.

The use of purified cucurbitacins in place of plant tissue is one possible solution to this problem, as purified cucurbitacin has been shown to be an effective feeding stimulant for diabroticite beetles in both adult and larval forms. Unfortunately, there are no products marketed today that utilize purified cucurbitacins. It would therefore be desirable to provide a simple, cost-effective and high-yield process for isolating and purifying cucurbitacin compounds in large quantities. It would also be desirable to use the cucurbitacins isolated in this manner in methods and formulations for the control of insects, particularly diabroticite beetles.

SUMMARY OF THE INVENTION

The present invention relates to a method of isolating and purifying cucurbitacins from plants. Accordingly, a first aspect of this invention is a method of isolating pure cucurbitacin from plant tissue by extraction with organic solvents and purification by first providing a liquid obtained from cucurbitacin-containing plant matter. The liquid is then extracted with a non-polar solvent to remove waxes, pigments, fatty acids, lipids and terpenes from the cucurbitacin-containing solution. The separated aqueous liquid is then extracted with a moderately polar solvent to provide an organic phase comprising a mixture of partially purified cucurbitacins. Finally, the cucurbitacins are isolated and purified from the organic phase. In a preferred embodiment of the invention, the cucurbitacins are purified by flash column chromatography.

A second aspect of the invention is a method of fractionally isolating and purifying Cucurbitacins B, D, and E individually from plant tissue. In this embodiment of the invention, the method described above is used to provide an organic phase comprising a mixture of cucurbitacins, which mixture is then purified, preferably by flash column chromatography. This purified mixture then is eluted with a solvent mixture to separate a fraction essentially comprising Cucurbitacin B from the purified mixture. The remaining mixture then is eluted with a second solvent mixture to separate a fraction essentially comprising Cucurbitacin D. The remaining solution is finally extracted with a third solvent mixture to separate a fraction consisting essentially of Cucurbitacin E.

The present invention provides several advantages over methods known in the prior art, in that the use of the non-polar solvent to remove undesired components of the plant tissue allows for a more purified and higher yield of isolated cucurbitacin than has been achieved in prior methods. Additionally, the present invention allows the practitioner to isolate separate forms of cucurbitacins. In that some species of beetles respond more strongly to certain forms of cucurbitacins, the present invention thus allows for more specific applications of cucurbitacins in the field of pest control.

BRIEF DESCRIPTION OF THE DRAWINGS

FIG. 1 is a schematic diagram of process steps representative of an embodiment of the present invention in which a mixture of cucurbitacins is isolated from plant material.

FIG. 2 is a schematic diagram of process steps representative of an embodiment of the present invention in which a specific forms of cucurbitacin are fractionally isolated from plant material.

DETAILED DESCRIPTION OF THE INVENTION

As summarized above, the present invention provides a method of isolating and purifying cucurbitacins (hereinafter the "active compounds") from cucurbitacin-containing plants, by extracting the cucurbitacin with at least one non-polar organic solvent and at least one moderately polar solvent, and then isolating the purified active compounds.

Referring now to FIG. 1, a cucurbitacin-containing liquid 30 obtained from plant material containing cucurbitacin is provided. In one embodiment of the invention, plant material containing cucurbitacin 10 is subjected to compression 20, such that the liquid 30 is produced. This liquid is then extracted with a non-polar solvent 40, such that an aqueous phase essentially free of fatty acids, lipids, waxes, pigments and terpenes is produced. After the non-polar organic phase is removed, the remaining aqueous phase is then extracted with a moderately polar solvent 50, providing an organic phase containing a mixture of partially purified active compounds. These active compounds then are separated 60 from the organic phase, and then collected 80.

As used herein, the term "plant matter" refers to any part of a cucurbitacin-containing plant, mature or immature plants, juices or extracts of the plants, and the plants in processed or unprocessed form. Cucurbitacin-containing plants include the plants of the Cucurbitaceae family, which contain over 900 species and 100 genera and are familiar to consumers as the wild gourds, squash, cucumbers and melons of the Cucurbita, Cucumis, Citrullus, Marah, Echinocystis, Lagenaria, Sicyos, Ecballium, and Bryonia genera. Particular species useful in the present invention the buffalo gourd (*Cucurbita foetidissima*), *C. andreana, C. cylindrata, C. ecuadorensis, C. gracilor, C. okeechobensis, C. lundelliana, C. martinezii, C. palmata, C. palmeri, C. pedatifolia, C. sororia,* and *C. texana.* Other plant families which include cucurbitacin-producing species include the Begoniaceae, Cruciferae, Datiscaceae, Desfontainiaceae, Elaeocarpacae, Polemoniaceae, Primulaceae, Rubiaceae, Sterculiaceae, Euphorbiaceae, and Scrophulariaceae families, which plants are also useful in the practice of the present invention. In a preferred embodiment of the invention, the plant matter is fruit from *Cucurbita andreana* or *Citrullus colocynthes* plants.

The liquid obtained from plant matter containing cucurbitacin may be obtained by any method known in the art, but is preferably obtained by compressing the plant material such that a liquid is produced directly from the plant matter. Plant matter may be compressed by any method known in the art, including by sausage stuffers, screw presses, rotary press drums, or squeezing apparatus. The plant matter may be cut, diced or otherwise reduced in size or partitioned prior to pressing. Pressing the plant matter provides a mostly aqueous liquid containing cucurbitacins and other plant compounds. The liquid is separated from the remaining pulp by any means known in the art (e.g., by pressing the plant material through a mesh or sieve apparatus). The resulting liquid is typically very clear and does not require additional filtration, although the skilled artisan may choose to filter the solution if desired.

The liquid obtained from the plant matter is then extracted with a non-polar solvent, using separation methods which will be known to one skilled in the art. As defined herein, the term "non-polar solvent" means any organic solvent with a polarity index (P', see L. R. Snyder, *J. Chromatogr. Sci.* 16, 223 (1978)) of not greater than 2.0, and preferably not greater than 1.6. Examples of such non-polar solvents include hexane, petroleum ether, and carbon tetrachloride, with hexane being particularly preferred. Mixtures of solvents may also be employed. The extraction with the non-polar solvent may be performed once, or may be repeated as required, in order to remove the waxes, pigments (e.g., chlorophyll, xanthophyll), high boiling terpenes, and apolar fatty acids and lipids which can interfere with cucurbitacin purification. After extraction, the aqueous liquid is collected.

After extraction with the non-polar solvent, the organic phase is removed and the remaining aqueous phase extracted with a moderately polar solvent. As defined herein, the term "moderately polar solvent" means any organic solvent with a polarity index of not less than 2.0 and not greater than 5.0, and preferably not greater than 4.5. These solvents exhibit some polarity, but are not miscible with water. Examples of such solvents include chloroform, methylene chloride, and ethyl acetate, with chloroform being particularly preferred. Mixtures of solvents may also be employed. These solvents have a high affinity for cucurbitacins. The extraction with the moderately polar solvent may be performed once, or may be repeated as desired. After the extraction, the organic phase is collected. The extraction step may be performed by any method known to the skilled artisan, including by percolation and sequential elution with solvent, or by counter-current extraction.

After extraction with the moderately polar solvent, the organic phase contains a mixture of partially purified cucurbitacins. The cucurbitacins are then isolated and separated from the organic phase by any separation method known to one skilled in the art, including evaporation, fractional distillation, column chromatography, and high-performance liquid chromatography (HPLC). Separation by column chromatography is preferred, with separation by silica gel chromatography being more preferred, and flash column chromatography by the method of W. C. Still et al. (*J. Org. Chem.* 43, 2923–2925 (1978)) being most preferred.

After the separation step, the cucurbitacin is collected by standard methods which are known to those skilled in the art. For example, the cucurbitacins may be collected within a solvent, or may be applied to a column and then eluted therefrom using known techniques. If desired, the final mixture of cucurbitacins may be dried by any known means (e.g., evaporation, drying under vacuum) to yield an essentially solid final product.

The resulting collected product will comprise a mixture of cucurbitacins in essentially pure form. The essentially pure cucurbitacin is at least 50% pure, more preferably will be at least 65% pure, and most preferably will be at least 80% pure. The final yield of cucurbitacin will be at least 0.5 grams of essentially pure cucurbitacin per kilogram of starting plant material, more preferably at least 0.75 grams of essentially pure cucurbitacin per kilogram of starting plant material, and most preferably at least 1.0 gram of essentially pure cucurbitacin per kilogram of starting plant material. In prior art methods, the presence of fatty acids and pigments in crude plant matter extracts resulted in much lower yields and purity levels. The yield of purified cucurbitacin and the level of purity of the cucurbitacin product provided by the method of the present invention represent a significant advantage over those provided by methods of the prior art.

The chemical structures of seventeen cucurbitacins are known, and are identified by letters: A, B, C, D, E, F, G, H, I, J, K, L, O, P, Q, R, and S. As used herein, the term "cucurbitacin" refers to any form of cucurbitacin, including those forms listed above, or to the glycosides of any of these forms. Specific forms of cucurbitacins are known to have varying potencies with regard to particular activities and effects. It is known that, for example, Cucurbitacins B and D are the most potent feeding stimulants for diabroticite beetles, while Cucurbitacin D exhibits anti-ovulatory activity in mice, and Cucurbitacins B, D, and E all exhibit cytotoxic and anti-tumor effects. See Miro, supra, at 165–67. It would be particularly useful, therefore, to be able to isolate specific forms of cucurbitacins individually.

Figure 2:
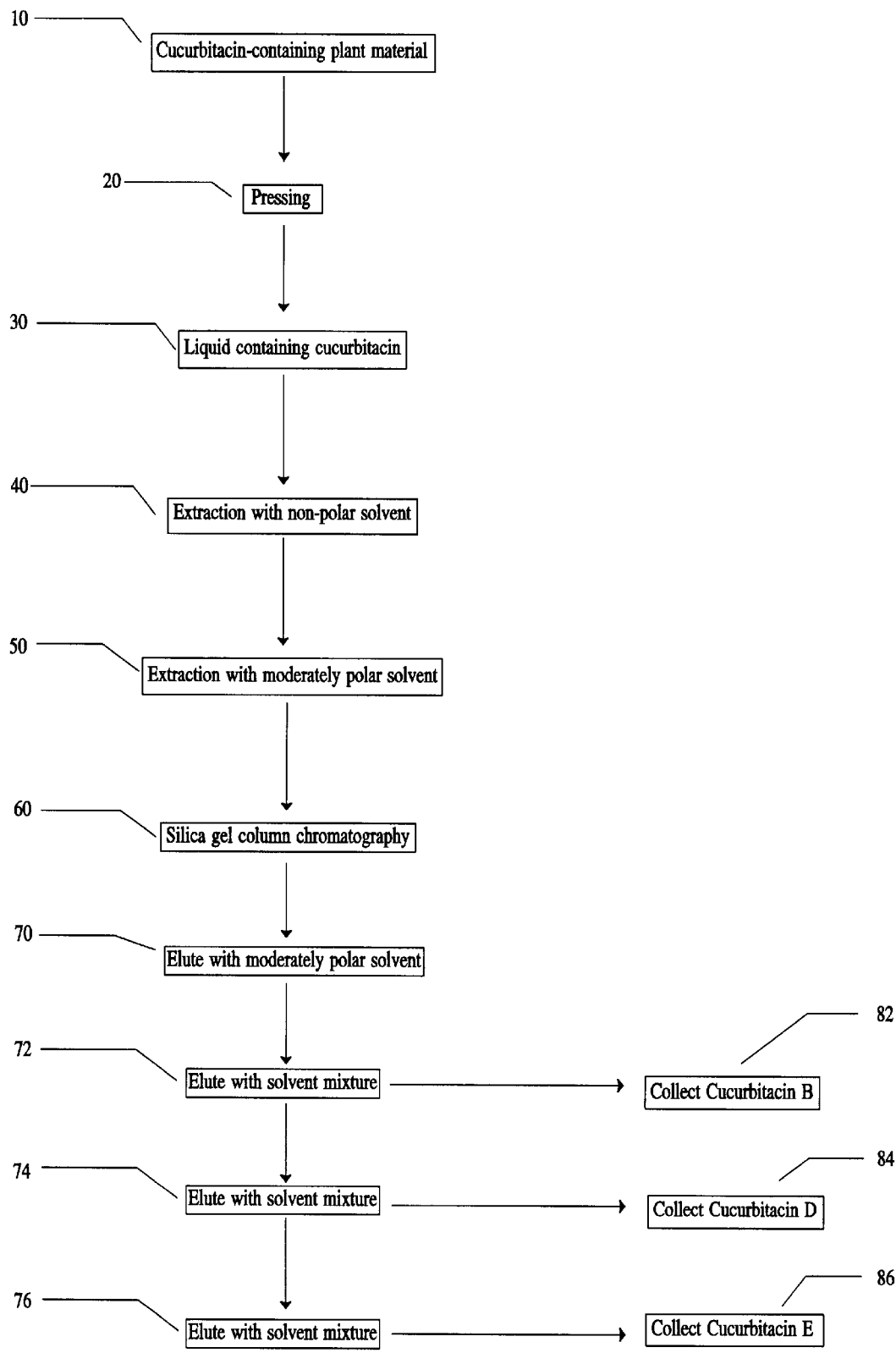

Accordingly, in another embodiment of the invention, specific forms of cucurbitacin are fractionally isolated. Referring now to FIG. 2, steps 10 through 50 are carried out in the same manner as described above and as illustrated in FIG. 1. After the organic phase containing the mixture of cucurbitacins is obtained, the organic phase is applied to a silica gel column for chromatography 60, and is preferably applied to a silica gel column useful in the flash column chromatography method. After application to the column, the column is first eluted with a moderately polar solvent (e.g., chloroform) 70, as described above. Next, the column is eluted with a suitable mixture of solvents (e.g., chloroform and acetone, toluene and acetone, ethyl acetate and acetone, or methylene chloride and acetone) 72, preferably in a ratio of about 95:5 by volume. This elution is collected 82, and essentially consists of the Cucurbitacin B fraction, which may then be additionally purified and dried by methods known in the art. Generally, the yield of Cucurbitacin B will be at least 100 mg per 1.0 gram of the starting cucurbitacin mixture (contained in the organic phase obtained after extraction with a moderately polar solvent), more preferably at least 200 mg per 1.0 gram of starting mixture, and most preferably at least 300 mg per 1.0 gram of starting mixture. The column is then eluted with a second suitable mixture of solvents (e.g., chloroform, acetone and methanol; ethyl acetate, acetone and methanol; or methylene chloride, acetone and methanol) 74, preferably in a ratio of about 90:5:5 by volume. This elution is collected 84, and essentially consists of the Cucurbitacin D fraction, which may then be additionally purified and dried by methods known in the art. Generally, the yield of Cucurbitacin D will be at least 100 mg per 1.0 gram of starting cucurbitacin mixture, more preferably at least 200 mg per 1.0 gram of the starting mixture, and most preferably at least 400 mg per 1.0 gram of the starting mixture. Finally, the silica gel column is eluted with a third suitable solvent mixture (e.g., chloroform, acetone and methanol; ethyl acetate, acetone and methanol; or methylene chloride, acetone and methanol) 76, preferably in a ratio of 80:5:15 by volume. This elution is collected 86, and essentially consists of the Cucurbitacin E fraction, which may then be additionally purified and dried by methods known in the art. Generally, the yield of Cucurbitacin E will be at least 5 mg per 1.0 gram of the starting cucurbitacin mixture, more preferably at least 10 mg per 1.0 gram of the starting mixture, and most preferably at least 20 mg per 1.0 gram of the starting mixture.

The skilled artisan will appreciate that solvents, separation methods, and elution methods not explicitly recited in the foregoing may be successfully utilized in the practice of the present invention, and that these alternate materials and methods may be determined without undue experimentation. Additionally, the skilled artisan will appreciate that cucurbitacin forms in addition to Cucurbitacins B, D, and E may be fractionally isolated by the method of the present invention, the isolation of which other forms will depend on the starting plant material, the related solubility of individual cucurbitacins, and the degree of separation possible between the individual cucurbitacins, determination of which can be made without undue experimentation.

The cucurbitacins isolated by the method of the present invention are useful as phagostimulants for diabroticite beetles, and as anti-feedants and toxins against other insects and herbivorous pests. Additionally, they are useful as therapeutic agents against fungal infections, inflammation, cancer and other maladies.

The present invention is more fully illustrated by the following examples, which are set forth to illustrate the present invention and are not to be construed as limiting thereof. In the following examples, L means liters, mL means millilters, g means grams, ng means nanograms, HPLC means high-performance liquid chromatography, and all temperatures are in degrees Centigrade.

EXAMPLE 1

Extraction and Purification of Cucurbitacin B and D

Mature *Cucurbita andreana* and *Citrullus colocynthes* fruits are harvested from fields and washed with water. Fruits are cut into four pieces and are pressed in a sausage stuffer (Lard presser, Chop-Rite Two Inc., Harleysville Pa.). The resulting solution (approximately 46% water content) is passed through cheese cloth and extracted sequentially with hexane and chloroform in a 4 L separating funnel. The chloroform fraction is dried under vacuum in a flash rotary evaporator at 40° C. and subjected to flash column chromatography according to the method of W. C. Still et al., *J. Organic Chem* 43, 2923–2925 (1978), to obtain a mixture of semi-purified cucurbitacin B, D, and E. The mixture is carried analyzed by analytic HPLC and semiprep HPLC, as follows.

Analytical HPLC: For high pressure liquid chromatography analysis, an HP 1090 liquid chromatogram is used, with a DR-5 solvent delivery system, variable volume autoinjector, autosampler, HP 1090 series diode array detector system and MS-DOS software. Three detection wavelengths (220, 254, and 340 nm) are used to scan the samples. A 100×2.1 mm column filled with C18 reverse phase gel is eluted with water and a linear gradient of 10–90% acetonitrile in 20 minutes at a flow rate of 0.5 ml/min.

Semi-prep HPLC: A Waters 715-Ultra WISP apparatus connected to a Waters 490 SENS (2.0 AUFS) multiwave detector is used. A C18 reverse phase semi-prep column (Vydoc) (10 μm) is eluted with water and a linear gradient of 10–90% acetonitrile in 60 min at a flow rate of 3.0 mL/min.

Confirmation and Identification by Direct Probe and Electrospray Mass Spectra. Cucurbitacin B and D are first analyzed by direct probe/electron impact mass spectrometry (EIMS). The results from these analysis cannot conclusively identify these samples as B and D. Two types of "soft ionization" are thus used to obtain the molecular ion: Electrospray (ES) and atmospheric pressure ionization (API). Both of these techniques can give the protonated molecular ion, [M+H]+. The API method does not give the expected results, but rather the loss of acetyloxy and or —OH groups giving a major ion at 499 with a sequential loss of the —OH groups (i.e. ions at m/z 481, 463, and 445). Both cucurbitacin B and D give similar ions and cannot be distinguished from each other.

The ES analysis does not give a molecular ion for both cucurbitacins B and D, but does provide a molecular ion spectrum for Cucurbitacin B. The cucurbitacin B gives ions at m/z 559.2 and 618.3 corresponding to [M+H]+ and [M+H2O+CH3CN]+, respectively. These molecular weights correspond to published literature values.

Activity of isolated cucurbitacin: Isolated cucurbitacin B and D are active as insect feeding stimulants at nanogram levels, as measured by the TLC scrap assay described by R. L. Metcalf et al., *Proc. Natl. Acad. Sci USA* 77, 3769–3772 (1980). 10 ng and 25 ng amounts of Cucurbitacin B and Cucurbitacin D are applied to a silica gel plate and placed in a chamber. When cucumber beetles are released into the chamber, the beetles are attracted to the cucurbitacin samples, completely consuming the samples and the silica gel attached to each sample.

EXAMPLE 2

Large-Scale Extraction and Purification of Cucurbitacin 400 pounds of *Cucurbita andreana* are hand-chopped and are then pressed in a screw press under 10 psi auger force. About 40 gallons of liquid are obtained from the pressing.

12.5 gallons of high purity hexane is added to 25 gal of the pressed melon liquid in a 50 gallon reactor equipped with agitator. The mixture is stirred slowly for 30 min, and allowed to separate for 30 min. After separating the hexane phase from the aqueous phase, the aqueous phase is retained in another tank, and the hexane extraction repeated for remainder of the melon liquid.

Next, 20 gallons of chloroform is added to 20 gallons of the hexane-extracted aqueous liquid in another 50 gallon reactor equipped with agitator. The mixture is stirred slowly for 30 minutes, and allowed to separate for 30 min. After separating the organic and aqueous phases, the organic phase is retained, and the chloroform extraction repeated with the remainder of the hexane-extracted melon liquid.

After chloroform extraction, the resulting organic phase is distilled to remove excess chloroform, and the remaining solution is dried in a large rotary evaporator to yield a mixture of purified cucurbitacins. After analysis, the resulting product is found to contain about 1.2 g of cucurbitacin per kilogram of starting plant material.

In the specification and examples, there have been disclosed preferred embodiments of the invention. Although specific terms are employed in these examples, they are used in a generic and descriptive sense only and not for the purpose of limitation, the scope of the invention being defined by the following claims.

That which is claimed is:

1. A method of fractionally isolating a cucurbitacin from *Cucurbita andreana*, comprising the steps of:
   (a) providing a cucurbitacin-containing liquid obtained from *Cucurbita andreana* plant matter containing cucurbitacin, whereby the cucurbitacin-containing liquid is obtained by compressing the *Cucurbita andreana* plant matter containing cucurbitacin to yield a liquid containing cucurbitacin;
   (b) extracting the cucurbitacin-containing liquid with at least one non-polar solvent to provide a cucurbitacin-containing solution;
   (c) extracting the solution produced in step (b) with at least one moderately polar solvent to provide an organic phase comprising a mixture of cucurbitacins;
   (d) separating the mixture of cucurbitacins from step (c) from the organic phase of step (c) using silica gel column chromatography;
   (e) eluting the separating column of step (d) with a mixture of solvents to yield a composition consisting of Cucurbitacin B; and
   (f) collecting the composition consisting of Cucurbitacin B.

2. A method according to claim 1, comprising the additional step of
   (i) eluting the column of step (d) with a mixture of solvents to yield a composition consisting of Cucurbitacin D; and
   (ii) collecting the composition consisting of Cucurbitacin D.

3. A method according to claim 1, comprising the additional step of
   (i) eluting the column of step (d) with a mixture of solvents to yield a composition consisting of Cucurbitacin E; and
   (ii) collecting the composition consisting of Cucurbitacin E.

4. A method according to claim whereby said separating step (d) is carried out using flash column chromatography.

5. The method according to claim 1, whereby the mixture of solvents comprises a mixture of chloroform and acetone in a proportion of about 95:5 by volume.

6. The method according to claim 2, whereby the mixture of solvents comprises chloroform, acetone and methanol in a proportion of about 90:5:5 by volume.

7. The method according to claim 3, whereby the mixture of solvents comprises chloroform, acetone and methanol in a proportion of about 80:5:15 by volume.

* * * * *

UNITED STATES PATENT AND TRADEMARK OFFICE
CERTIFICATE OF CORRECTION

PATENT NO. : 5,925,356
DATED : July 20, 1999
INVENTOR(S) : Ven Subbiah

It is certified that error appears in the above-identified patent and that said Letters Patent is hereby corrected as shown below:

Col. 8, Line 56, after "claim" insert --1--.

Signed and Sealed this

Nineteenth Day of September, 2000

Attest:

Q. TODD DICKINSON

Attesting Officer  Director of Patents and Trademarks